United States Patent
Chassaing et al.

(10) Patent No.: US 12,018,020 B2
(45) Date of Patent: Jun. 25, 2024

(54) CRYSTALLINE FORMS OF 1-[(3R,4S)-4-CYANOTETRAHYDROPYRAN-3-YL]-3-[(2-FLUORO-6-METHOXY-4-PYRIDYL)AMINO]PYRAZOLE-4-CARBOXAMIDE

(71) Applicant: Intervet Inc., Madison, NJ (US)

(72) Inventors: Christophe Pierre Alain Chassaing, Ingelheim am Rhein (DE); Xiaoling Jin, Green Brook, NJ (US); Rositza Iordanova Petrova, Metuchen, NJ (US); Richard J. Varsolona, Scotch Plains, NJ (US); Lorenzo Codan, Olten (CH); Edward Cleator, Whittlesford (GB); Adrian Goodyear, Buntingford (GB); Jonathan Simmons, Ware (GB); Tanja Schweisel, Arbach (DE)

(73) Assignee: Intervet Inc., Rahway, NJ (US)

( * ) Notice: Subject to any disclaimer, the term of this patent is extended or adjusted under 35 U.S.C. 154(b) by 586 days.

(21) Appl. No.: 17/311,560

(22) PCT Filed: Dec. 12, 2019

(86) PCT No.: PCT/EP2019/084898
§ 371 (c)(1),
(2) Date: Jun. 7, 2021

(87) PCT Pub. No.: WO2020/120679
PCT Pub. Date: Jun. 18, 2020

(65) Prior Publication Data
US 2022/0024902 A1 Jan. 27, 2022

(30) Foreign Application Priority Data
Dec. 13, 2018 (EP) ...................................... 18212191

(51) Int. Cl.
*C07D 405/14* (2006.01)
(52) U.S. Cl.
CPC ........ *C07D 405/14* (2013.01); *C07B 2200/13* (2013.01)
(58) Field of Classification Search
CPC .......................... C07D 405/14; C07B 2200/13
See application file for complete search history.

(56) References Cited

FOREIGN PATENT DOCUMENTS

| WO | 2013041042 A1 | 3/2013 | |
|----|---------------|--------|---|
| WO | 2018108969 A1 | 6/2018 | |
| WO | WO-2018108969 A1 * | 6/2018 | ......... A61K 31/4439 |

OTHER PUBLICATIONS

Byrn, Stephen, et al., Pharmaceutical Solids: A Strategic Approach to Regulatory Considerations, Pharmaceutical Research, 1995, p. 945-954, vol. 12, No. 7.
Siu T et al, The discovery of 3-((4-chloro-3-methoxyphenyl)amino)-1-((3R,4S)-4-cyanotetrahydro-2H-pyran-3-yl)-1H-pyrazole-4-carboxamide, a highly ligand efficient and efficacious janus kinase 1 selective inhibitor with favorable pharmacokinetic properties, Journal of Medicinal Chemistry, 2017, pp. 9676-9690, vol. 60, No. 23.
Bernstein, J., Bioavailability, Polymorphism of molecular crystals, 2007, 324-330 (translated pp. 1-9), Ch. 7.3.2.
Bernstein, J., Bioavailability, Polymorphism of molecular crystals, 2007, 324-330, Ch. 7.3.2.
Caira, Crystalline Polymorphism of organic compounds, Topics in Current Chemistry, 1998, 163-208, 198.
Hirayama, N.,, Handbook of Preparation of Organic Compound Crystals, 2008, pp. 17-23, 37-40, 45-51, 57-65, Kodansha.
Hirayama, Noriaki, Handbook for Fabrication of Organic Compound Crystals, Handbook for Fabrication of Organic Compound Crystals, 2008, 3 pages, N/A, Kodansha, partial translation.
Kummerer, K., Pharmaceuticals in the environment, Annual Review of Environment and Resources, 2010, 57-75, 35.
Kuznetsova, G.A., Methodological instructions, Irkutsk State University (Seihveisu), Department of General Physics, 2005, 1, N/A, English translation.
Kuznetsova, G.A., Methodological instructions, Irkutsk State University (Seihveisu), Department of General Physics, 2005, 1-2, N/A.
Rodriquez-Spong, Barbara et al., General principles of pharmaceutical solid polymorphism: a supramolecular perspective, Advanced Drug Delivery Reviews, 2004, 241-274, 56.
Sarma, Bipul et al., Solid forms of pharmaceuticals: Polymorphs, salts and cocrystals, Korean J. Chem. Eng., 2011, 315-322, 28(2).
Variankaval, Narayan et al., From Form to Function: Crystallization of Active Pharmaceutical Ingredients, AIChE Journal, 2008, 1682-1688, 54(7).

* cited by examiner

*Primary Examiner* — Bahar Craigo
*Assistant Examiner* — Manahil Mirghani Ali Abdalhameed
(74) *Attorney, Agent, or Firm* — David J. Kerwick (57) ABSTRACT

The present application relates to crystalline forms of 1-[(3R,4S)-4-cyanotetrahydropyran-3-yl]-3-[(2-fluoro-6-methoxy-4-pyridyl) amino]pyrazole-4-carboxamide and processes for the preparation thereof. The compound is useful for the treatment of JAK-mediated diseases or conditions such as atopic dermatitis.

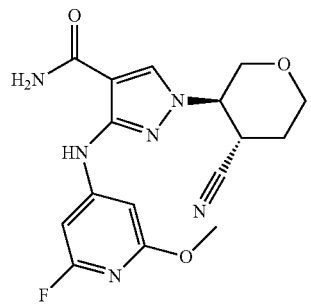

15 Claims, 9 Drawing Sheets

FIG.1

FIG.2 Solid state C-13 CPMAS NMR spectrum for Form 1. Peaks labeled with asterisks correspond to spinning sidebands.

Solid state C-13 CPMAS NMR spectrum for Hydrate. Peaks labeled with asterisks correspond to spinning sidebands.

FIG. 9

CRYSTALLINE FORMS OF 1-[(3R,4S)-4-CYANOTETRAHYDROPYRAN-3-YL]-3-[(2-FLUORO-6-METHOXY-4-PYRIDYL)AMINO]PYRAZOLE-4-CARBOXAMIDE

CROSS-REFERENCE TO RELATED APPLICATIONS

This application is a national stage entry under 35 U.S.C. § 371 of PCT/EP2019/084898 filed on Dec. 12, 2019, which claims priority to EP18212191.3 filed on Dec. 13, 2018, the content of PCT/EP2019/084898 is hereby incorporated by reference in its entirety.

BACKGROUND

WO 2018/108969 discloses compounds of formula I which are selective Janus kinase (JAK) inhibitors, and as such are useful for the treatment of JAK-mediated diseases such as atopic dermatitis, arthritis, and cancer. Specifically, 1-[(3R,4S)-4-cyanotetrahydropyran-3-yl]-3-[(2-fluoro-6-methoxy-4-pyridyl)amino]pyrazole-4-carboxamide (I) is disclosed.

Formula I

This reference also discloses that the above compound was produced as a yellow solid.

WO 2013/041042 discloses pyrazole carboxamides as Janus kinase inhibitors that are useful for the treatment of rheumatoid arthritis, asthma, chronic obstructive pulmonary disease (COPD) and cancer. The compounds of this disclosure are of the following formula

SUMMARY OF THE INVENTION

A crystalline form (Form 1) of 1-[(3R,4S)-4-cyanotetrahydropyran-3-yl]-3-[(2-fluoro-6-methoxy-4-pyridyl)amino]pyrazole-4-carboxamide having at least one of the following characteristics:

an X-ray powder diffraction (XRPD) pattern having at least one peak selected from the group consisting of 6.9, 13.9, 17.8, 19.6, 20.4, 20.9, 24.7, 25.0, 26.6 and 29.1 degrees 2θ (±0.2)

a carbon-13 cross-polarization magic-angle spinning (CP-MAS) nuclear magnetic resonance (NMR) spectrum having at least one peak selected from the group consisting of signals at 30.61, 32.60, 53.40 59.59, 67.21, 71.93, 88.50, 96.35, 104.47, 120.39, 121.95, 131.45, 153.31, 161.41, 163.36, and 166.70 ppm.

or a differential scanning calorimetry (DSC) thermogram comprising an endothermic peak at about 257(±1)° C.

DETAILED DESCRIPTION

1-[(3R,4S)-4-cyanotetrahydropyran-3-yl]-3-[(2-fluoro-6-methoxy-4-pyridyl)amino]pyrazole-4-carboxamide has been found to exist in three crystalline forms, Form 1 and Form 2 as well as a hydrate.

The polymorphic Form 1 and Form 2 of 1-[(3R,4S)-4-cyanotetrahydropyran-3-yl]-3-[(2-fluoro-6-methoxy-4-pyridyl)amino]pyrazole-4-carboxamide are monotropically related. Form 1 is the themodynamically most stable form at all temperatures.

There are several advantages of the Form 1 polymorph crystals over Form 2 polymorph crystals. First, it's the thermodynamically most stable form. In addition, Form 1 carries lower risk of conversion to hydrate under humid conditions.

An embodiment of the invention is a crystalline form (Form 1) of 1-[(3R,4S)-4-cyanotetrahydropyran-3-yl]-3-[(2-fluoro-6-methoxy-4-pyridyl)amino]pyrazole-4-carboxamide (I) having at least one of the following characteristics:

an X-ray powder diffraction (XRPD) pattern having at least one peak in terms of degrees 2θ (±0.2) selected from the group consisting of 6.9, 13.9, 17.8, 19.6, 20.4, 20.9, 24.7, 25.0, 26.6 and 29.1;

a carbon-13 cross-polarization magic-angle spinning (CP-MAS) nuclear magnetic resonance (NMR) spectrum having at least one peak selected from the group consisting of signals at 30.61, 32.60, 53.40, 59.59, 67.21, 71.93, 88.50, 96.35, 104.47, 120.39, 121.95, 131.45, 153.31, 161.41, 163.36, and 166.70 ppm;

or
a differential scanning calorimetry (DSC) thermogram comprising an endothermic peak at about 257 (±1) ° C.

In an embodiment, the crystalline Form 1 has an X-ray powder diffraction (XRPD) pattern comprising peaks in terms of degrees 2θ (±0.2) at 6.7, 13.9 and 19.9.

In an embodiment, the crystalline Form 1 has a X-ray powder diffraction (XRPD) pattern further comprising peaks in terms of degrees 2θ (±0.2) at 5.0, a doublet peak at 20.4 and 20.9 and a doublet peak at 22.2 and 22.6.

In an embodiment, the crystalline Form 1 has a X-ray powder diffraction (XRPD) pattern further comprising a peak set in terms of degrees 2θ (±0.2) at 24.7, 26.6 and 29.1.

Figure 1:
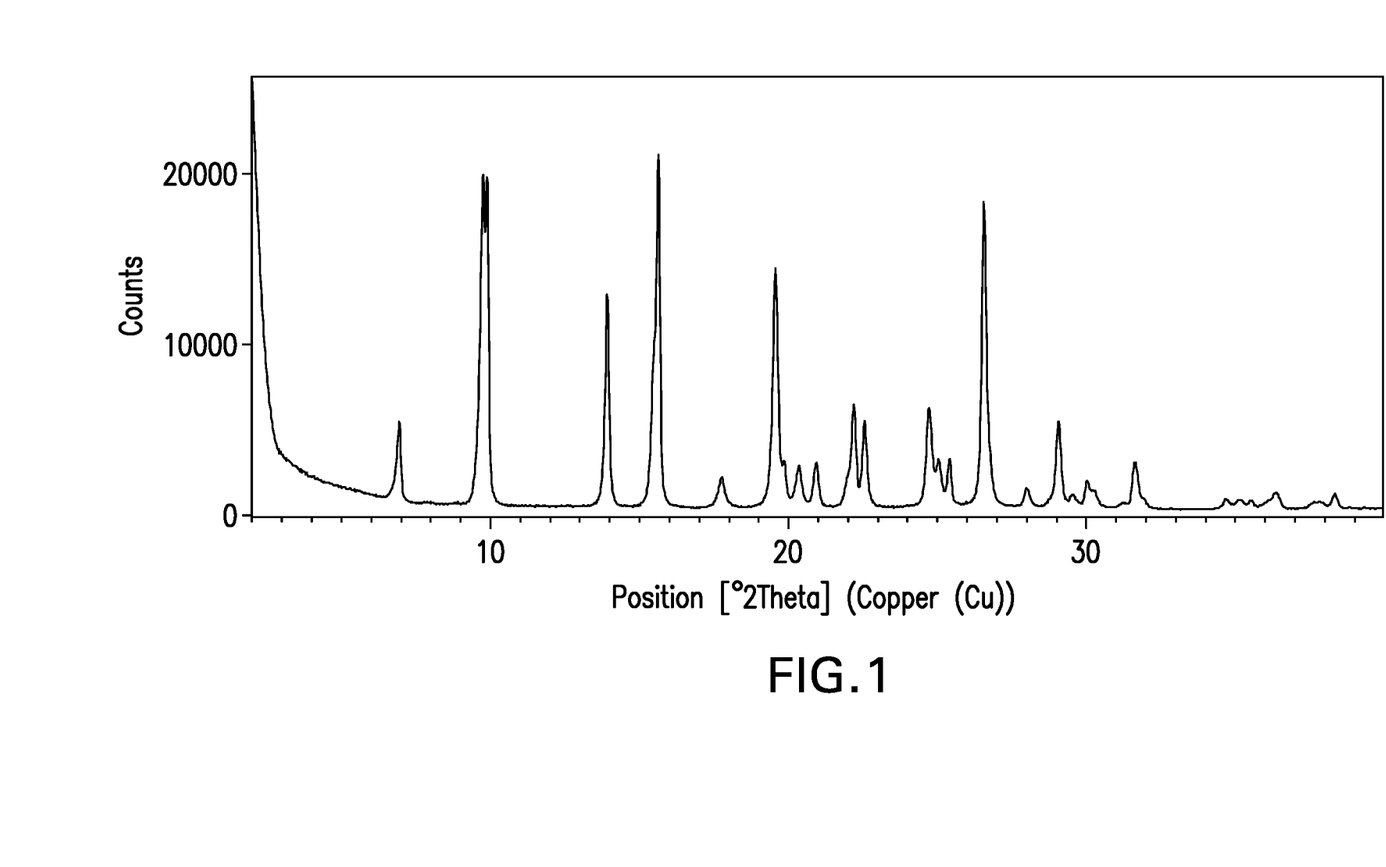
FIG. 1 is a is a characteristic X-ray powder diffraction pattern of the crystalline Form 1

In an embodiment, the crystalline Form 1 has an X-ray powder diffraction (XRPD) pattern substantially as shown in FIG. 1.

Figure 2:
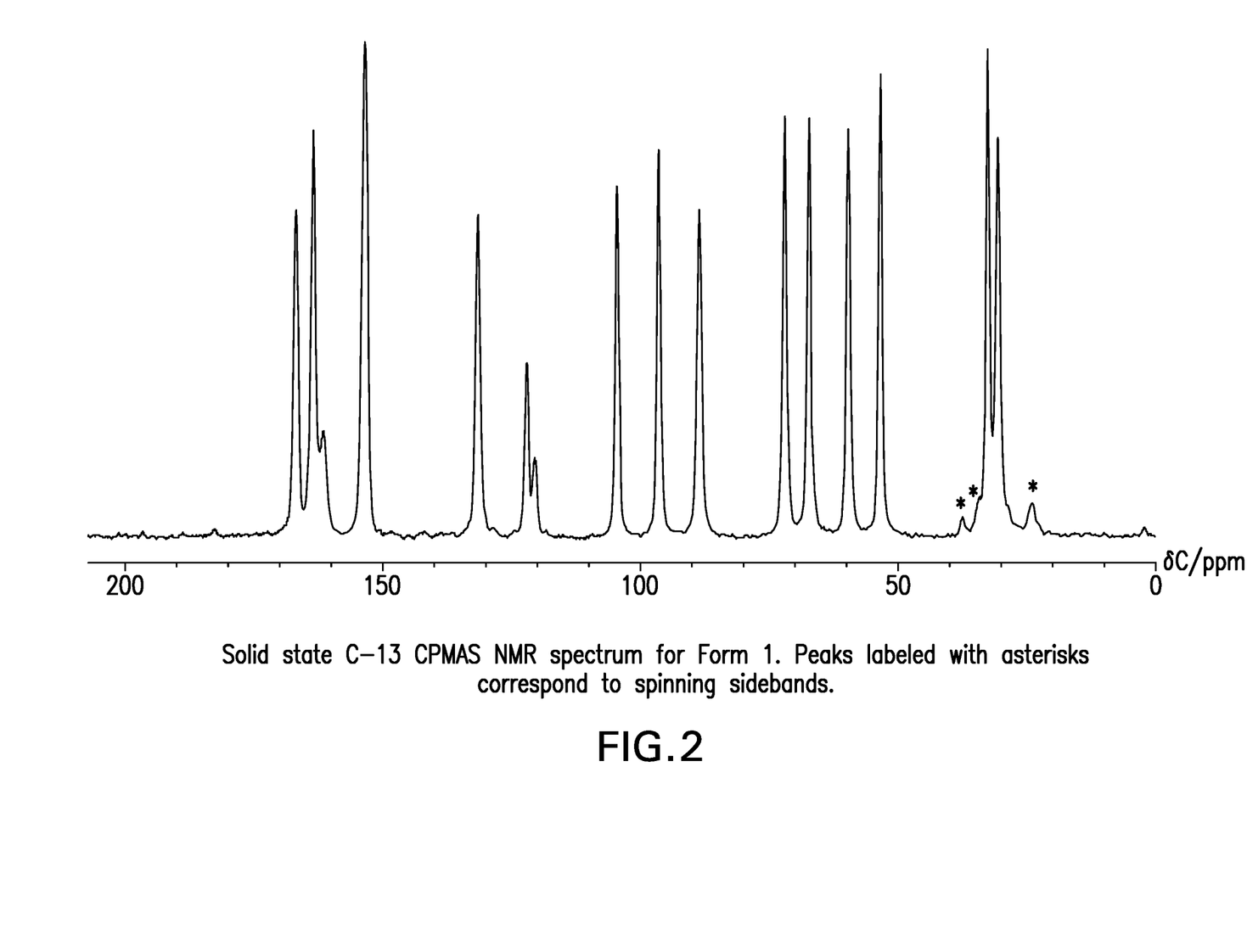
FIG. 2 is a carbon-13 cross-polarization magic-angle spinning (CPMAS) nuclear magnetic resonance (NMR) spectrum of the crystalline Form 1. Peaks labeled with asterisks correspond to spinning sidebands.

In an embodiment, the crystalline Form 1 has a carbon-13 cross-polarization magic-angle spinning (CPMAS) nuclear magnetic resonance (NMR) spectrum substantially as shown in FIG. 2.

Figure 3:
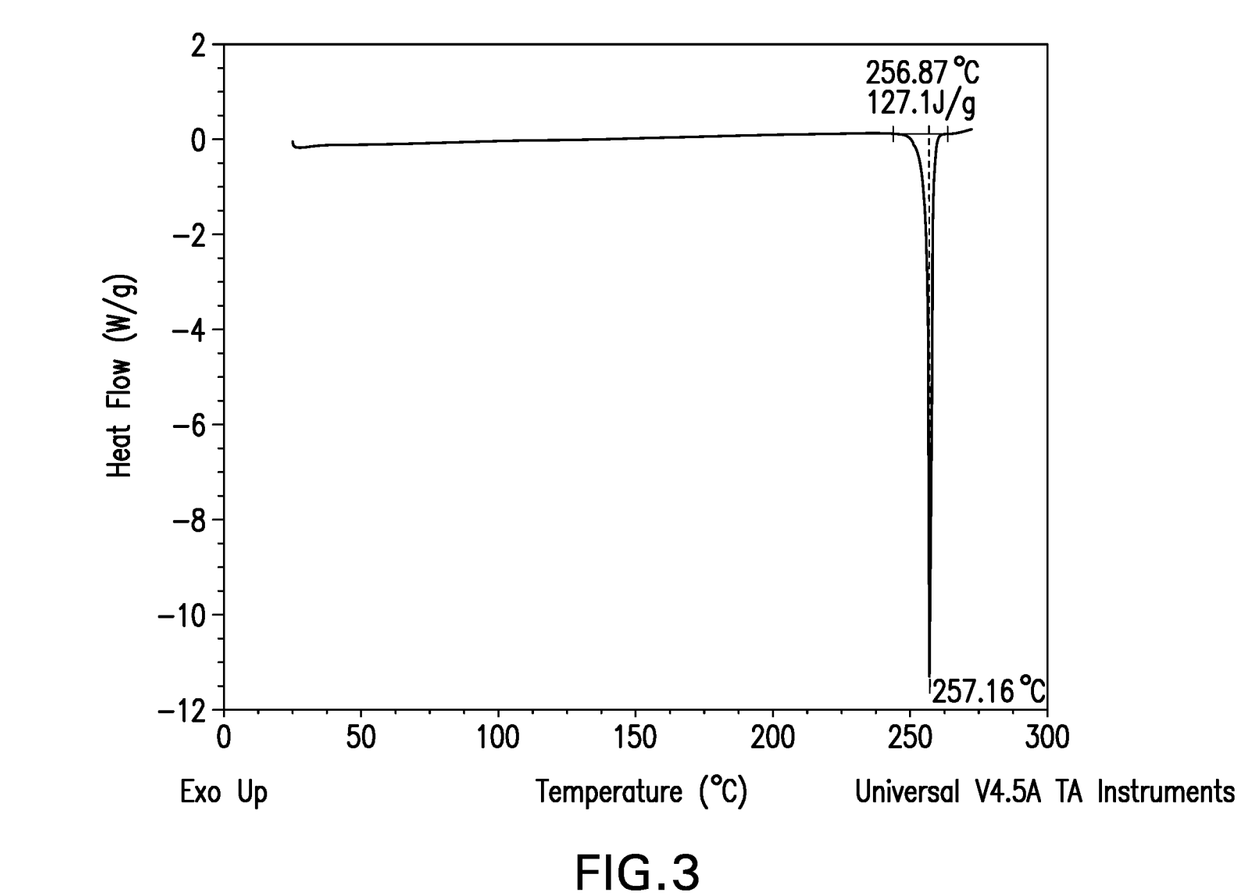
FIG. 3 is a typical DSC thermogram of the crystalline Form 1.

In an embodiment, the crystalline Form 1 has a differential scanning calorimetry (DSC) thermogram substantially as shown in FIG. 3.

Another embodiment of the invention is a crystalline form (Form 2) of 1-[(3R,4S)-4-cyanotetrahydropyran-3-yl]-3-[(2-fluoro-6-methoxy-4-pyridyl)amino]pyrazole-4-carboxamide (I) having at least one of the following characteristics:
an X-ray powder diffraction (XRPD) pattern having at least one peak in terms of degrees 2θ (±0.2) selected from the group consisting of 6.3, 7.9, 12.7, 14.9, 15.1, 16.9 and 17.1;
a carbon-13 cross-polarization magic-angle spinning (CPMAS) nuclear magnetic resonance (NMR) spectrum having at least one peak selected from the group consisting of signals at 29.39, 30.67, 32.06, 52.40, 54.80, 59.92, 65.57, 67.64, 71.01, 72.30, 88.52, 92.33, 93.02, 103.96, 121.32, 122.79, 130.85, 152.10, 162.16, 163.05, 164.45, and 168.12 ppm;
or
a differential scanning calorimetry (DSC) thermogram comprising an endothermic peak at about 252 (±2) ° C.

In an embodiment, the crystalline Form 2 has a X-ray powder diffraction (XRPD) pattern comprising peaks in terms of degrees 2θ (±0.2) at 6.3, 7.9 and 12.7.

In an embodiment, the crystalline Form 2 has a X-ray powder diffraction (XRPD) pattern further comprising peaks in terms of degrees 2θ (±0.2) a doublet peak at 14.9 and 15.1 and a doublet peak at 16.9 and 17.1.

Figure 4:
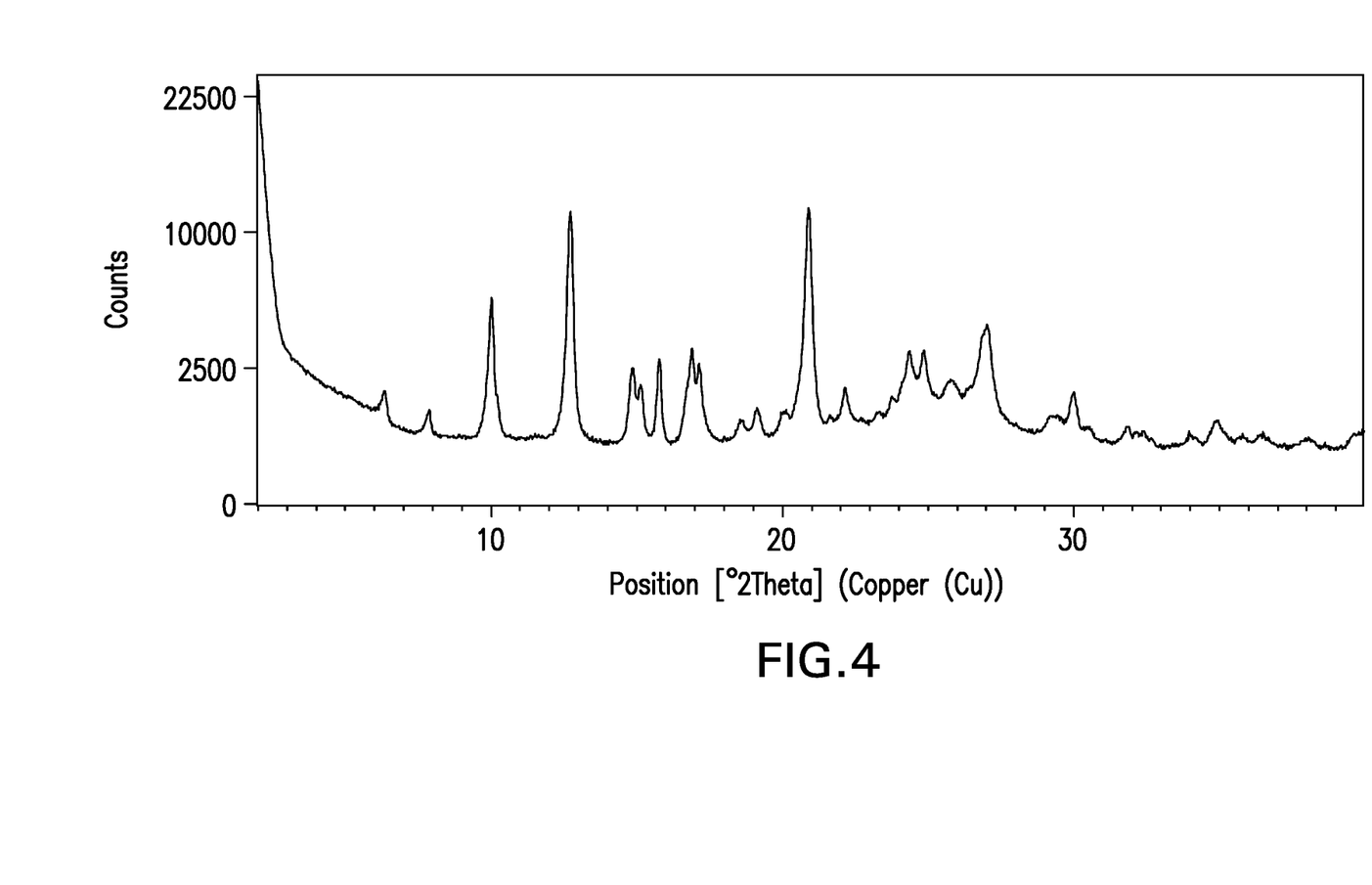
FIG. 4 is a is a characteristic X-ray powder diffraction pattern of the crystalline Form 2

In an embodiment, the crystalline Form 2 has an X-ray powder diffraction (XRPD) pattern substantially as shown in FIG. 4.

Figure 5:
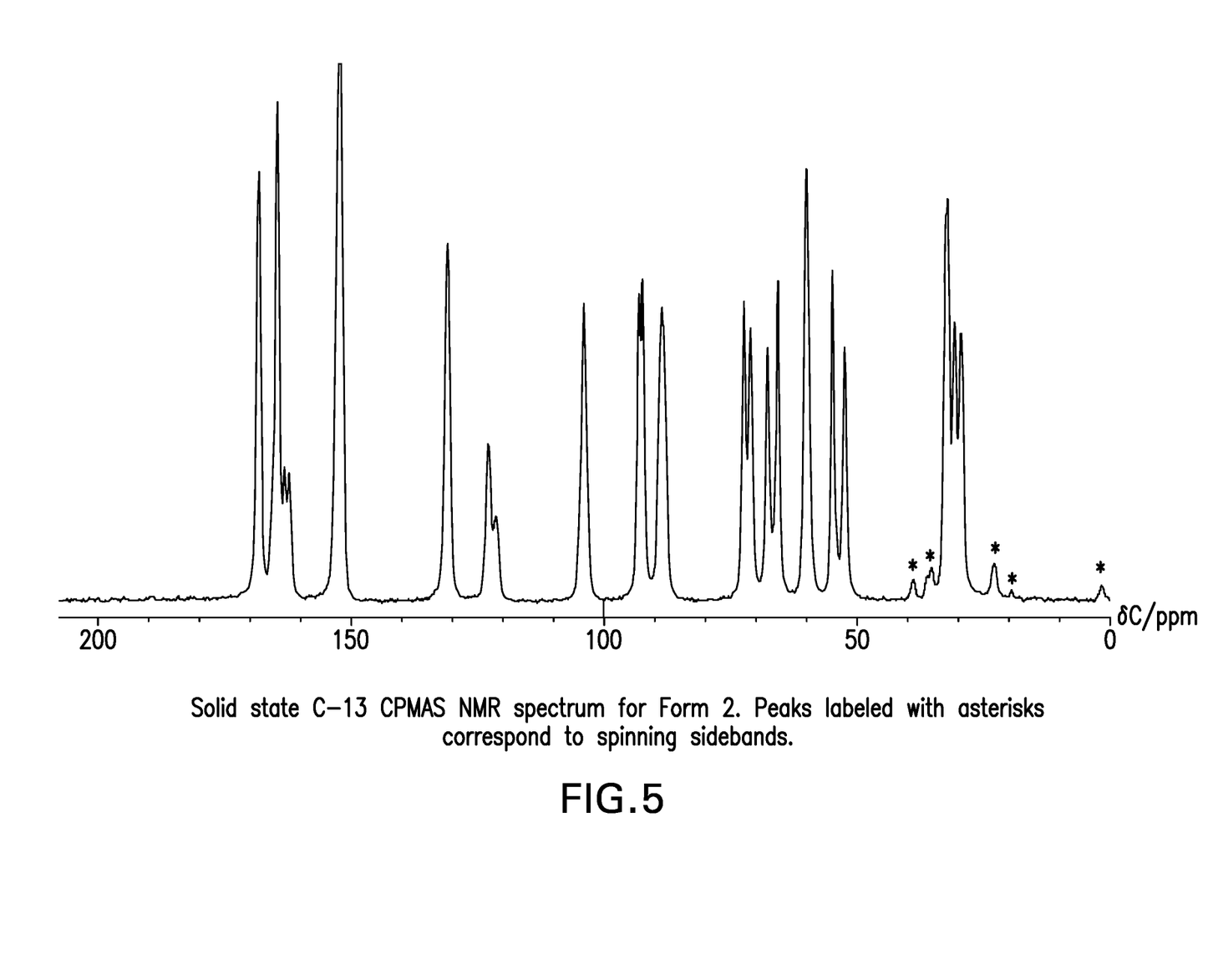
FIG. 5 is a carbon-13 cross-polarization magic-angle spinning (CPMAS) nuclear magnetic resonance (NMR) spectrum of the crystalline Form 2. Peaks labeled with asterisks correspond to spinning sidebands.

In an embodiment, the crystalline Form 2 has carbon-13 cross-polarization magic-angle spinning (CPMAS) nuclear magnetic resonance (NMR) spectrum substantially as shown in FIG. 5.

Figure 6:
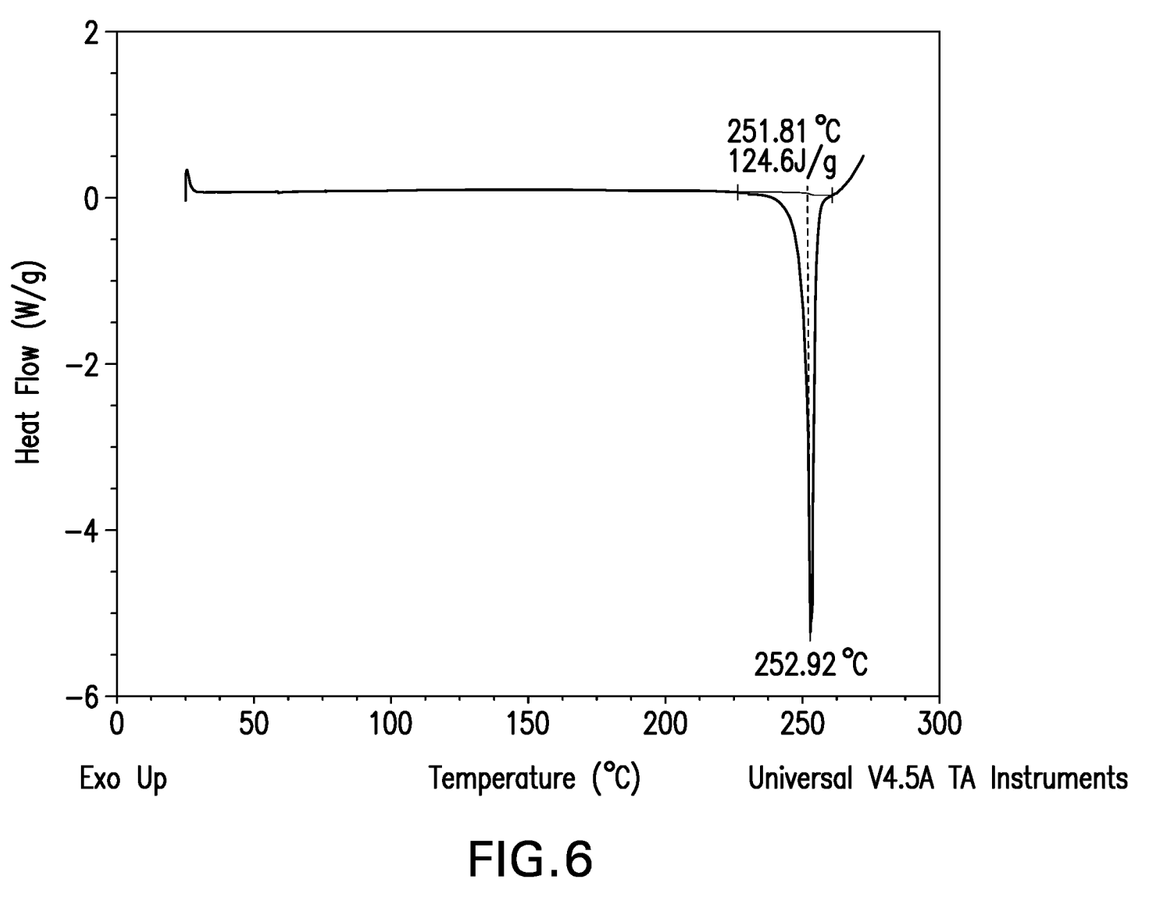
FIG. 6 is a typical DSC thermogram of the crystalline Form 2.

In an embodiment, the crystalline Form 2 has a differential scanning calorimetry (DSC) thermogram substantially as shown in FIG. 6.

Another embodiment of the invention is a crystalline hydrate form of 1-[(3R,4S)-4-cyanotetrahydropyran-3-yl]-3-[(2-fluoro-6-methoxy-4-pyridyl)amino]pyrazole-4-carboxamide (I) having at least one of the following characteristics:
an X-ray powder diffraction (XRPD) pattern having at least one peak selected from the group consisting of peaks in terms of degrees 2θ (±0.2) at 7.3, 12.6, 12.9, 13.1, 16.2, 17.4, 21.8, 27.8 and 28.4;
a carbon-13 cross-polarization magic-angle spinning (CPMAS) nuclear magnetic resonance (NMR) spectrum having at least one peak selected from the group consisting of signals at 29.80, 30.52, 54.35, 60.67, 65.45 70.62, 89.08, 92.52, 102.17, 121.96, 123.48, 131.05, 152.21, 163.46, 164.53, and 168.40 ppm;
or
a differential scanning calorimetry (DSC) thermogram comprising a first endothermic peak with an onset temperature of about 27° C. and a second endothermic peak at about 254(±2) ° C.

In an embodiment, the crystalline hydrate form has an X-ray powder diffraction (XRPD) pattern comprising peaks in terms of degrees 2θ (±0.2) at 7.3, a triplet at 12.6, 12.9 and 13.1 and a peak at 17.4.

In an embodiment, the crystalline hydrate form has a X-ray powder diffraction (XRPD) pattern further comprising peaks in terms of degrees 2θ (±0.2) at 16.2, 21.8, 27.8 and 28.4.

Figure 7:
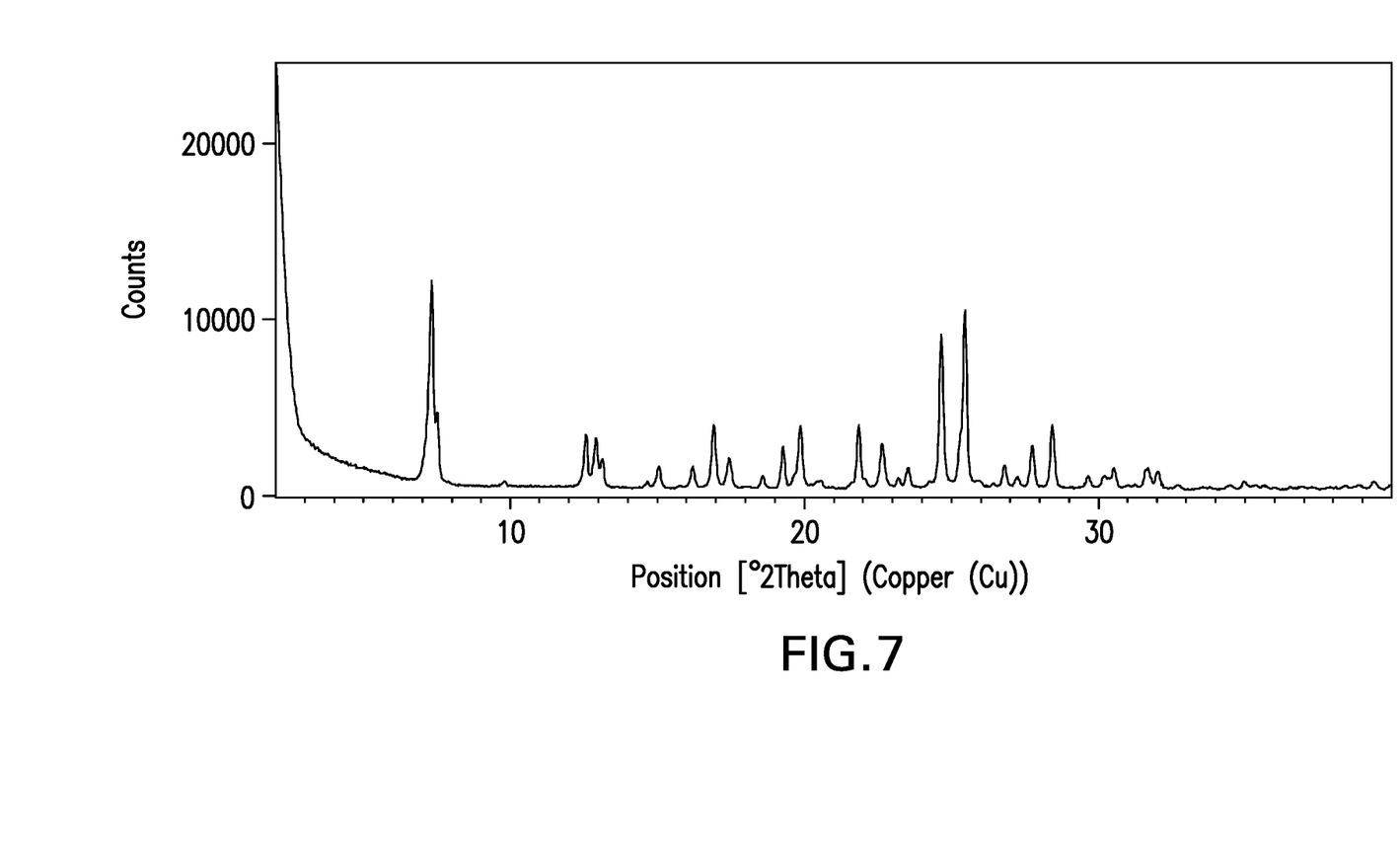
FIG. 7 is a is a characteristic X-ray powder diffraction pattern of the crystalline hydrate form.

In an embodiment, the crystalline hydrate form has an X-ray powder diffraction (XRPD) pattern substantially as shown in FIG. 7.

Figure 8:
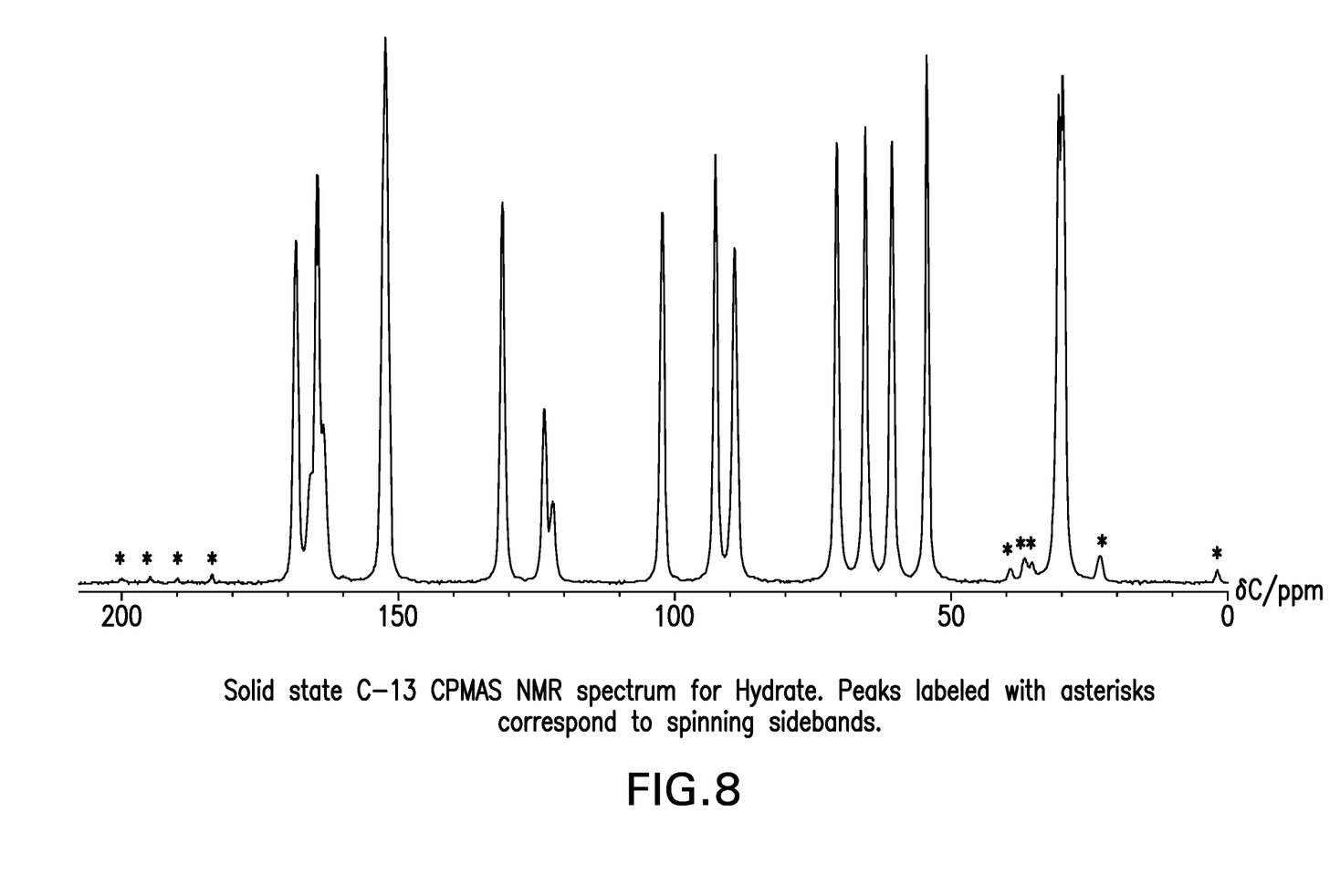
FIG. 8 is a carbon-13 cross-polarization magic-angle spinning (CPMAS) nuclear magnetic resonance (NMR) spectrum of the crystalline hydrate form. Peaks labeled with asterisks correspond to spinning sidebands.

In an embodiment, the crystalline hydrate form has a carbon-13 cross-polarization magic-angle spinning (CPMAS) nuclear magnetic resonance (NMR) spectrum substantially as shown in FIG. 8.

Figure 9:
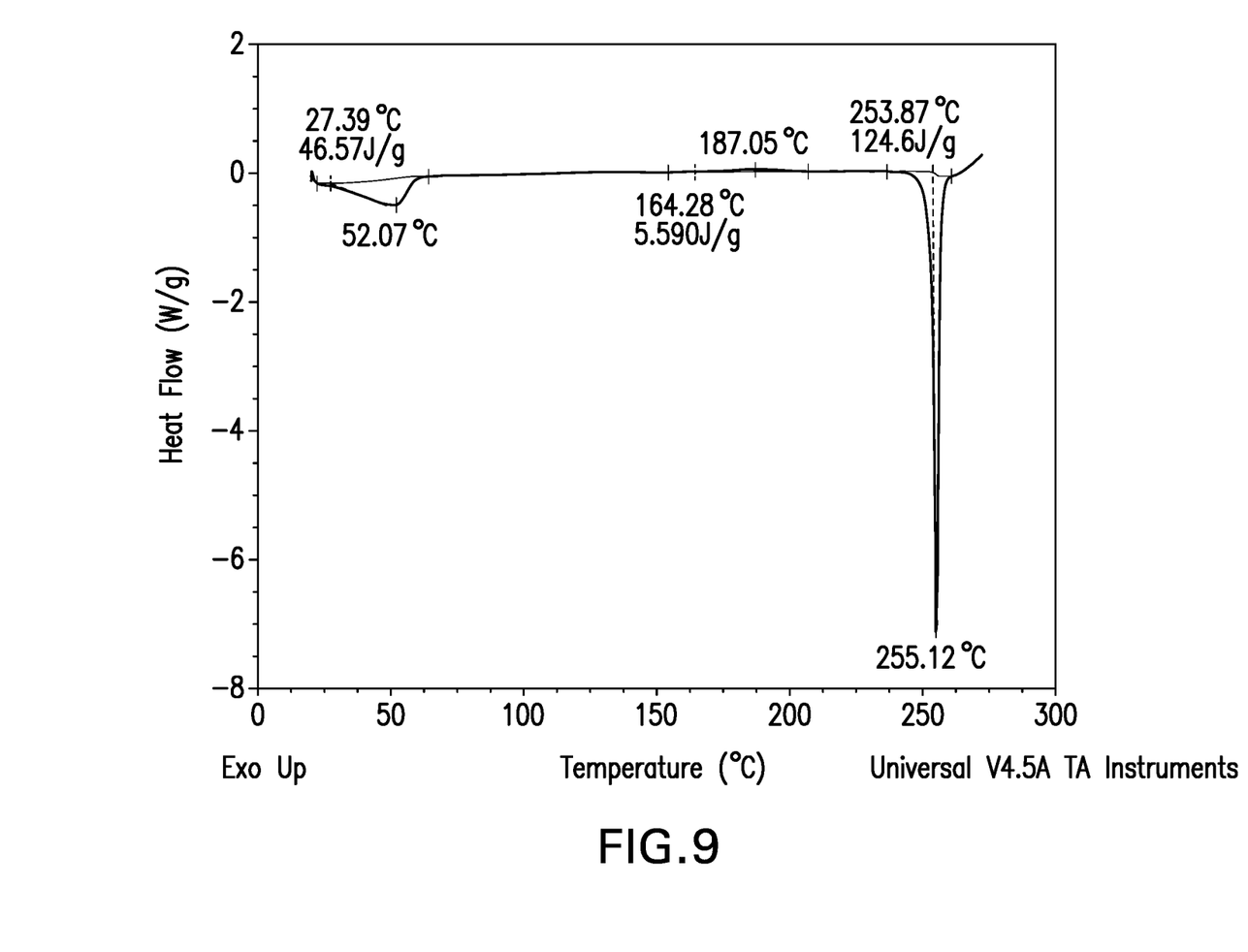
FIG. 9 is a typical DSC thermogram of the crystalline hydrate form.

In an embodiment, the crystalline hydrate form has a having a differential scanning calorimetry (DSC) thermogram substantially as shown in FIG. 9.

Another embodiment is a pharmaceutical composition comprising the anyone of the above crystalline forms and a pharmaceutical excipient.

An embodiment of the pharmaceutical composition wherein the crystalline form is substantially purified.

Another embodiment is a method of treating or preventing a JAK-mediated disease or condition in a mammal comprising administering anyone of the above compositions.

In an embodiment, the JAK-mediated disease or condition is atopic dermatitis.

Another embodiment is a process for preparing the crystalline form of anyone of claims 1-12 comprising either precipitating the crystalline form from a solution or by heating a slurry of 1-[(3R,4S)-4-cyanotetrahydropyran-3-yl]-3-[(2-fluoro-6-methoxy-4-pyridyl)amino]pyrazole-4-carboxamide (I) and by optionally inducing formation of the desired form by seeding the mixture with seeds of the desired form.

In an embodiment, the solvent or mixture of solvents is selected from the group consisting of methanol, DMAc, toluene, xylenes and ethyl acetate or mixtures thereof.

In an embodiment of the above process, a quantity of crystalline form seeds are added to the solution or slurry. In another embodiment, the quantity of seeds is from about 0.1% to about 10.0%, preferably about 1.0 to about 5.0% of the weight of the 1-[(3R,4S)-4-cyanotetrahydropyran-3-yl]-3-[(2-fluoro-6-methoxy-4-pyridyl)amino]pyrazole-4-carboxamide (I).

In an embodiment of the above process, the solution or slurry is heated to reflux. In another embodiment, the solvent is added in portions.

In an embodiment of the above process, the reflux temperature is between about 60° C. and about 70° C. and the solution is cooled to a temperature of lower then about 25° C.

Dimethylacetamide (DMAc or DMA) is an organic compound of formula $CH_3C(O)N(CH_3)_2$ which is commonly used as a solvent.

It is anticipated that the crystalline hydrate has the advantage of being more stable in an aqueous containing formulation than a non-hydrated crystalline form.

The term "substantially as shown" as used herein refers to an X-ray powder diffraction (XRPD) spectrum, carbon-13 cross-polarization magic-angle spinning (CPMAS) nuclear magnetic resonance (NMR) spectrum, or differential scanning calorimetry (DSC) thermogram that is non-identical to those depicted herein, but may fall within the limits of experimental error, when considered by one of ordinary skill in the art. One of ordinary skill in the art would understand that an X-ray powder diffraction spectrum may contain peaks that fall within ±0.2 degrees 2Θ of the peaks contained in the spectrum of FIG. 1 and a differential scanning calorimetry (DSC) thermogram as depicted in FIG. 3 may contain an endotherm at ±3° C. of what is depicted.

The term "substantially purified" as used herein refers to a crystalline form of the compound that is at least 90% pure. In an alternate embodiment, "substantially purified" refers to a crystalline form of the compound that is at least 95%, 99%, or 99.9% pure.

EXAMPLES

Samples of Forms 1 and 2 and the hydrate Form were prepared as described below.

Example 1—Form 1

1A

A 160 L glass-lined vessel was charged with 1-[(3R,4S)-4-cyanotetrahydropyran-3-yl]-3-[(2-fluoro-6-methoxy-4-pyridyl)amino]pyrazole-4-carboxamide (3.72 kg, 10.32 mol) and methanol (80.8 L). The contents were heated to reflux (65° C.) and authentic 1-[(3R,4S)-4-cyanotetrahydropyran-3-yl]-3-[(2-fluoro-6-methoxy-4-pyridyl)amino]pyrazole-4-carboxamide Form 1 seeds (109 g, 302.5 mmol) charged as a slurry in methanol (1.9 L). The Form I seeds were obtained via slurry to slurry turnover in refluxing methanol (30 volumes). The mixture was stirred at 275 rpm and aged for 14.5 h. The slurry was cooled from 65° C. to 20° C. over 12 h and then aged at 20° C. for 6 h.

The batch was filtered and the wet cake was washed with methanol (5.4 L). The solid was dried at 40° C. for 23 h in a vacuum oven with a nitrogen bleed. The material was then passed through a Co-Mill to break up any lumps and 1-[(3R,4S)-4-cyanotetrahydropyran-3-yl]-3-[(2-fluoro-6-methoxy-4-pyridyl)amino]pyrazole-4-carboxamide Form 1 (2.21 kg, 6.14 mol) was obtained as a white powder.

1B

Crude API (150 g) was purified and obtained as a hydrate. The hydrate was then stirred in methanol at reflux with 5% form 1 seed for 14 hours. The slurry was sampled at reflux for XRPD, which indicated a small amount of form 2 was present (<5%). The slurry was cooled to 20° C. and wet milled for 30 minutes at 5200 rpm using an IKA Ultra Turrax wetmill. It was then returned to reflux for another 16 hours.

After sampling at reflux, XRPD indicated form 2 was still present, albeit at a significantly reduced level. So the slurry was cooled to 20° C. and wet milled again for 30 minutes at 5200 rpm. It was then returned to reflux for another 16 hours.

This time XRPD indicated the material was 100% form 1. The slurry was cooled to 20° C. over 12 hours and then aged at 20° C. for 6 hours. The material was reconfirmed as form 1 before filtration and drying. A total of 109 g form 1 API was obtained as an off-white powder (82% recovery corrected for assay).

1C

1-[(3R,4S)-4-cyanotetrahydropyran-3-yl]-3-[(2-fluoro-6-methoxy-4-pyridyl)amino]pyrazole-4-carboxamide (52 g) was diluted with N,N-dimethylacetamide (170 mL) and methanol (52 mL). The resulting slurry was stirred at a temperature between 20 and 25° C. for 5 to 10 min at 400 rpm. The mixture was heated to 60° C. When the temperature reached 52° C., the mixture turned clear and became a solution.

A and additional methanol (61 mL) was added to the solution which was further stirred at 60° C. for 5 to10 min. Seeds (260 mg or 0.5% of total api) of Form 1 of 1-[(3R,4S)-4-cyanotetrahydropyran-3-yl]-3-[(2-fluoro-6-methoxy-4-pyridyl)amino]pyrazole-4-carboxamide were added and a slurry immediately formed. Agitation was increased to 500 rpm and methanol (661 mL) was added over 10 h. The obtained slurry was aged at 60° C., and then cooled to 0° C. over 5 h. The slurry was milled for 60 min, aged for 2 hours at 0° C. and then filtered. The isolated product was washed with methanol (2×160 mL) and then dried under vacuum at room temperature for 2 hours followed by drying in a vacuum oven at 50° C. for 16 hours. 46.6 g of Form 1 crystals obtained.

Example 2—Form 2

Form 2 was obtained as described in WO 2018/108969.

Example 3—Hydrate

3A

Form 2 (0.2 g) was slurried in water (10 mL) at RT for 14 days. The suspension was then filtered and vacuum dried at ambient condition (0.18 g isolated). Hydrate formation was confirmed by PXRD.

3B

Form 2 (0.1 g) was slurried in 70/30 (v/v) MeOH/H2O (2 mL) at RT for 1 day. The suspension was then filtered and vacuum dried at ambient condition (X g isolated). Hydrate formation was confirmed by PXRD Each of these samples of Forms 1 and 2 and the hydrate were characterized as described below:

The X-Ray Powder Diffraction (XRPD)

X-ray powder diffraction studies are widely used to characterize molecular structures, crystallinity, and polymorphism. The X-ray powder diffraction patterns of Form 1 and Form 2 and of the hydrate were generated on Bruker AXS D8 Advance with a LYNXEYE XE-T detector in reflection mode.

Solid State NMR

In addition to the X-ray powder diffraction patterns described above, Form 1, 2 and hydrate samples were further characterized based on their carbon-13 solid-state nuclear magnetic resonance (NMR) spectrum. The carbon-13 spectrum was recorded on a Bruker AV400 NMR spectrometer operating at a carrier frequency of 400.14 MHz, using a Bruker 4 mm H/F/X BB triple resonance CPMAS probe. The spectrum was collected utilizing proton/carbon-13 variable-amplitude cross-polarization (VACP) at 80 kHz, with a contact time of 3 ms. Other experimental parameters used for data acquisition were a proton 90-degree pulse of 100 kHz, SPINAL64 decoupling at 100 kHz, a pulse delay of 30.0 s, and signal averaging for 2900 scans. The magic-angle spinning (MAS) rate was set to 13 kHz. A Lorentzian line broadening of 30 Hz was applied to the spectrum before Fourier Transformation. Chemical shifts are reported on the TMS scale using the carbonyl carbon of glycine (176.70 ppm) as a secondary reference.

Differential Scanning Calorimetry (DSC)

DSC data were acquired using TA Instruments DSC Q2000 or equivalent instrumentation. A sample with a weight between 1 and 6 mg is weighed into an open pan. This pan is placed in the sample position in the calorimeter cell. An empty pan is placed in the reference position. The calorimeter cell is closed and a flow of nitrogen is passed through the cell. The heating program is set to heat the sample at a heating rate of 10° C./min to a temperature of approximately 275° C. When the run is completed, the data are analyzed using the DSC analysis program in the system software. The observed endo- and exotherms are integrated between baseline temperature points that are above and below the temperature range over which the endotherm or exotherm is observed. The data reported are the onset temperature, peak temperature and enthalpy.

Physical Characterization of 1-[(3R,4S)-4-cyanotetrahydropyran-3-yl]-3-[(2-fluoro-6-methoxy-4-pyridyl)amino]pyrazole-4-carboxamide Crystalline Form 1

FIG. 1 shows the X-ray powder diffraction pattern of Form 1. Form 1 exhibited characteristic diffraction peaks corresponding to d-spacings of 12.7, 6.4, and 4.5 angstroms. Form 1 was further characterized by the d-spacings of 5.0, a doublet peak at 4.4 and 4.2 angstroms and another doublet peak at 4.0 and 3.9 angstroms. Form 1 was even further characterized by the d-spacings of a peak set at 3.6, 3.4, and 3.1 angstroms.

TABLE 1

Characteristic Peak Position and Corresponding d-Spacing for crystalline Form 1

| Peak Position [°2θ] | d-Spacing [Å] |
| --- | --- |
| 6.9 | 12.7 |
| 9.7 | 9.1 |
| 9.9 | 9.0 |
| 13.9 | 6.4 |
| 15.5 | 5.7 |
| 15.6 | 5.7 |
| 17.8 | 5.0 |
| 19.6 | 4.5 |
| 19.9 | 4.5 |
| 20.4 | 4.4 |
| 20.9 | 4.2 |
| 22.2 | 4.0 |
| 22.6 | 3.9 |
| 24.7 | 3.6 |
| 25.0 | 3.6 |
| 25.4 | 3.5 |
| 26.6 | 3.4 |
| 28.0 | 3.2 |
| 29.1 | 3.1 |
| 29.5 | 3.0 |
| 30.0 | 3.0 |
| 30.2 | 3.0 |
| 31.2 | 2.9 |
| 31.6 | 2.8 |
| 34.7 | 2.6 |
| 35.1 | 2.6 |
| 35.5 | 2.5 |
| 36.4 | 2.5 |
| 37.7 | 2.4 |
| 37.8 | 2.4 |
| 38.3 | 2.3 |

Form 1 was characterized based on its solid-state carbon-13 nuclear magnetic resonance (NMR) spectrum (see FIG. 2). The carbon-13 spectrum was recorded on a Bruker AV400 NMR spectrometer operating at a carrier frequency of 400.14 MHz, using a Bruker 4 mm H/F/X BB triple resonance CPMAS probe. The spectrum was collected utilizing proton/carbon-13 variable-amplitude cross-polarization (VACP) at 80 kHz, with a contact time of 3 ms. Other experimental parameters used for data acquisition were a proton 90-degree pulse of 100 kHz, SPINAL64 decoupling at 100 kHz, a pulse delay of 30.0 s, and signal averaging for 2900 scans. The magic-angle spinning (MAS) rate was set to 13 kHz. A Lorentzian line broadening of 30 Hz was applied to the spectrum before Fourier Transformation. Chemical shifts are reported on the TMS scale using the carbonyl carbon of glycine (176.70 ppm.) as a secondary reference.

Characteristic carbon-13 isotropic chemical shifts for Form 1 are observed at 30.61, 32.60, 53.4022, 59.59, 67.21, 71.93, 88.50, 96.35, 104.47, 120.39, 121.95, 131.45, 153.31, 161.41, 163.36, and 166.70 ppm.

FIG. 3 is a typical DSC thermogram of the crystalline Form 1. The DSC thermogram is characterized by a melting endotherm with an extrapolated onset temperature of 256.9° C., a peak temperature of 257.2° C. and enthalpy of 127.1 J/g.

Physical Characterization of 1-[(3R,4S)-4-cyanotetrahydropyran-3-yl]-3-[(2-fluoro-6-methoxy-4-pyridyl)amino]pyrazole-4-carboxamide Crystalline Form 2

FIG. 4 shows the X-ray powder diffraction pattern of 1-[(3R,4S)-4-cyanotetrahydropyran-3-yl]-3-[(2-fluoro-6-methoxy-4-pyridyl)amino]pyrazole-4-carboxamide Crystalline Form 2 exhibited characteristic diffraction peaks corresponding to d-spacings of 13.9, 11.2, and 7.0 angstroms. Form 2 was further characterized by the d-spacings of a doublet peak at 6.0 and 5.9 angstroms and another doublet peak at 5.3 and 5.2 angstroms.

TABLE 2

Characteristic Peak Position and Corresponding d-Spacing for crystalline Form 2

| Peak Position [°2θ] | d-Spacing [Å] |
| --- | --- |
| 6.3 | 13.9 |
| 7.9 | 11.2 |
| 10.0 | 8.8 |
| 12.7 | 7.0 |
| 14.9 | 6.0 |
| 15.1 | 5.9 |
| 15.8 | 5.6 |
| 16.9 | 5.3 |
| 17.1 | 5.2 |
| 18.6 | 4.8 |
| 19.1 | 4.6 |
| 20.1 | 4.4 |
| 20.9 | 4.3 |
| 22.1 | 4.0 |
| 23.3 | 3.8 |
| 23.8 | 3.7 |
| 24.4 | 3.7 |
| 24.8 | 3.6 |
| 25.8 | 3.5 |
| 27.0 | 3.3 |
| 29.2 | 3.1 |
| 30.0 | 3.0 |
| 31.8 | 2.8 |
| 32.4 | 2.8 |

TABLE 2-continued

Characteristic Peak Position and Corresponding
d-Spacing for crystalline Form 2

| Peak Position [°2θ] | d-Spacing [Å] |
|---|---|
| 34.0 | 2.6 |
| 34.9 | 2.6 |
| 35.8 | 2.5 |
| 36.4 | 2.5 |
| 38.0 | 2.4 |
| 39.6 | 2.3 |

Form 2 was characterized based on its solid-state carbon-13 nuclear magnetic resonance (NMR) spectrum (see FIG. 5). The carbon-13 spectrum was recorded on a Bruker AV400 NMR spectrometer operating at a carrier frequency of 400.14 MHz, using a Bruker 4 mm H/F/X BB triple resonance CPMAS probe. The spectrum was collected utilizing proton/carbon-13 variable-amplitude cross-polarization (VACP) at 80 kHz, with a contact time of 3 ms. Other experimental parameters used for data acquisition were a proton 90-degree pulse of 100 kHz, SPINAL64 decoupling at 100 kHz, a pulse delay of 17.0 s, and signal averaging for 5916 scans. The magic-angle spinning (MAS) rate was set to 13 kHz. A Lorentzian line broadening of 30 Hz was applied to the spectrum before Fourier Transformation. Chemical shifts are reported on the TMS scale using the carbonyl carbon of glycine (176.70 ppm.) as a secondary reference.

Characteristic carbon-13 isotropic chemical shifts for Form 2 are observed at 29.39, 30.67, 32.06, 52.40, 54.80, 59.92, 65.57, 67.64, 71.01, 72.30 88.52, 92.33, 93.02, 103.96, 121.32, 122.79, 130.85, 152.10, 162.16, 163.05, 164.45, and 168.12 ppm.

FIG. 6 is a typical DSC thermogram of the crystalline Form 2. The DSC thermogram is characterized by a melting endotherm with an extrapolated onset temperature of 251.8° C., a peak temperature of 252.9° C. and enthalpy of 124.6 J/g.

Physical Characterization of 1-[(3R,4S)-4-cyanotetrahydropyran-3-yl]-3-[(2-fluoro-6-methoxy-4-pyridyl)amino]pyrazole-4-carboxamide crystalline hydrate form FIG. 7 shows the X-ray powder diffraction pattern of 1-[(3R,4S)-4-cyanotetrahydropyran-3-yl]-3-[(2-fluoro-6-methoxy-4-pyridyl)amino]pyrazole-4-carboxamide crystalline hydrate form exhibited characteristic diffraction peaks corresponding to d-spacings of 12.1, a triplet peak at 7.0, 6.9 and 6.7 angstroms and a peak at 5.1 angstroms. The hydrate form was further characterized by the d-spacings of 5.5, 4.1, 3.2 and 3.1 angstroms.

TABLE 3

Characteristic Peak Position and Corresponding
d-Spacing for crystalline hydrate.

| Peak Position [°2θ] | d-Spacing [Å] |
|---|---|
| 7.3 | 12.1 |
| 7.5 | 11.8 |
| 9.8 | 9.0 |
| 12.6 | 7.0 |
| 12.9 | 6.9 |
| 13.1 | 6.7 |
| 14.7 | 6.0 |
| 15.0 | 5.9 |
| 15.8 | 5.6 |
| 16.2 | 5.5 |
| 16.9 | 5.2 |
| 17.4 | 5.1 |
| 18.6 | 4.8 |
| 19.3 | 4.6 |
| 19.9 | 4.5 |
| 20.6 | 4.3 |
| 21.8 | 4.1 |
| 22.6 | 3.9 |
| 23.2 | 3.8 |
| 23.5 | 3.8 |
| 24.3 | 3.7 |
| 24.7 | 3.6 |
| 25.3 | 3.5 |
| 25.5 | 3.5 |
| 25.9 | 3.4 |
| 26.4 | 3.4 |
| 26.8 | 3.3 |
| 27.2 | 3.3 |
| 27.8 | 3.2 |
| 28.4 | 3.1 |
| 29.7 | 3.0 |
| 30.2 | 3.0 |
| 30.5 | 2.9 |
| 31.2 | 2.9 |
| 31.6 | 2.8 |
| 31.7 | 2.8 |
| 32.0 | 2.8 |
| 32.7 | 2.7 |
| 33.6 | 2.7 |
| 34.5 | 2.6 |
| 35.0 | 2.6 |
| 35.3 | 2.5 |
| 35.6 | 2.5 |
| 36.9 | 2.4 |
| 38.4 | 2.3 |
| 38.9 | 2.3 |
| 39.4 | 2.3 |

The hydrate was characterized based on its solid-state carbon-13 nuclear magnetic resonance (NMR) spectrum. The carbon-13 spectrum was recorded on a Bruker AV400 NMR spectrometer operating at a carrier frequency of 400.14 MHz, using a Bruker 4 mm H/F/X BB triple resonance CPMAS probe. The spectrum was collected utilizing proton/carbon-13 variable-amplitude cross-polarization (VACP) at 80 kHz, with a contact time of 3 ms. Other experimental parameters used for data acquisition were a proton 90-degree pulse of 100 kHz, SPINAL64 decoupling at 100 kHz, a pulse delay of 1.6 s, and signal averaging for 8000 scans. The magic-angle spinning (MAS) rate was set to 13 kHz. A Lorentzian line broadening of 30 Hz was applied to the spectrum before Fourier Transformation. Chemical shifts are reported on the TMS scale using the carbonyl carbon of glycine (176.70 ppm.) as a secondary reference.

Characteristic carbon-13 isotropic chemical shifts for the hydrate are observed at 29.80, 30.52, 54.35, 60.67, 65.45, 70.62, 89.08, 92.52, 102.17, 121.96, 123.48, 131.05, 152.21, 163.46, 164.53, and 168.40 ppm.

FIG. 9 is a typical DSC curve of the crystalline hydrate form. The DSC curve is characterized by two endotherms and one exotherm. The first endotherm with an extrapolated onset temperature of 27.4° C., a peak temperature of 52.1° C., and enthalpy of 46.6 J/g is due to dehydration. The exotherm with an extrapolated onset temperature of 164.1°

C. is due to solid phase transition to Form 2. The endotherm with an extrapolated onset temperature of 253.9° C., a peak temperature of 255.1° C. and enthalpy of 124.6 J/g is due to melting of Form 2.

Relative Thermodynamic Stability of Form 1, Form 2 and Hydrate

Form 1 and Form 2 are monotropically related. Form 1 is more stable than Form 2. Hydrate is the most stable form in aqueous solutions.

Processability Assessment for Form 1 and Form 2

Both Form 1 and Form 2 are physically and chemically stable after 12 months of storage at 40° C./75% relative humidity (RH) and 55° C. There is a risk of Form 2 conversion to hydrate at the typical wet granulation temperature when seeds of hydrate are present. Small scale crystallization process studies demonstrated that Form 1 can be consistently delivered.

Form 1 remained as Form 1 after slurried in MeOH for 3 weeks at room temperature (RT). When ~10 mg each of Form 1 and Form 2 were slurried in 1 mL of MeOH at 50° C., full conversion to Form 1 was observed after 4 days.

When Form 2 was slurried in 2-Me-THF, Ethyl Acetate, MeOH or MeOH/toluene (70:30 v/v) at 50° C., seeded with Form 1 at 14 days and equilibrated for an additional 14 days (28 days total), full or conversion to Form 1 was observed. Partial conversion was observed after 28 days in Ethyl Acetate and Isopropyl Acetate at 25° C. This is evidence that Form 1 is more thermodynamically stable than Form 2.

The lower solubility of Form 1 than Form 2 also indicated that Form 1 is the more stable form:

| | In 7/3 v/v toluene/MeOH | |
|---|---|---|
| Temperature (° C.) | Solubility (mg/mL) Form 1 | Form 2 |
| 25 | 3.4 | 4.7 |
| 40 | 6.6 | 9.3 |
| 60 | 12.5 | 15.6 |

Conversion to Hydrate Risk

Slurry experiments in water containing 5% SLS were used to assess the risk of form conversion during wet granulation. Typical wet granulation conditions include drying at 60 to 70° C. for 1.5 to 2 hours.

Slurries containing 20 mg/mL of either Form 1 or Form 2 in 5% sodium lauryl sulfate (SLS) aqueous solution were seeded with 5% hydrate seeds and monitored for form change with PXRD over 24 hours at room temperature and at 80° C. No hydrate peak growth observed for Form 1 samples, indicating that Form 1 is stable for 24 hours in the presence of the hydrate at RT and 80° C. While no hydrate peak growth was observed for the Form 2 samples at 80° C., hydrate peak growth was observed for Form 2 samples at RT. This indicates that Form 2 is not stable in the presence of hydrate seeds at RT. These results indicated that the risk of form conversion to hydrate is lower for Form 1 than for Form 2 when hydrate seeds are present.

The invention claimed is:

1. A crystalline form (Form 1) of 1-[(3R,4S)-4-cyanotetrahydropyran-3-yl]-3-[(2-fluoro-6-methoxy-4-pyridyl)amino]pyrazole-4-carboxamide having at least one of the following characteristics:

an X-ray powder diffraction (XRPD) pattern having at least one peak in terms of ° 2θ(±0.2) selected from the group consisting of 6.9, 13.9, 17.8, 19.6, 20.4, 20.9, 24.7, 25.0, 26.6 and 29.1;
   a carbon-13 cross-polarization magic-angle spinning (CP-MAS) nuclear magnetic resonance (NMR) spectrum having at least one peak selected from the group consisting of 30.61, 32.60, 53.40, 59.59, 67.21, 71.93, 88.50, 96.35, 104.47, 120.39, 121.95, 131.45, 153.31, 161.41, 163.36, and 166.70 ppm;
   or
   a differential scanning calorimetry (DSC) thermogram comprising an endothermic peak at about 257° C.

2. The crystalline form of claim 1, having an X-ray powder diffraction (XRPD) pattern substantially as shown in FIG. 1.

3. The crystalline form of claim 1, having carbon-13 cross-polarization magic-angle spinning (CPMAS) nuclear magnetic resonance (NMR) spectrum substantially as shown in FIG. 2.

4. The crystalline form of claim 1, having a differential scanning calorimetry (DSC) thermogram substantially as shown in FIG. 3.

5. A crystalline hydrate form of 1-[(3R,4S)-4-cyanotetrahydropyran-3-yl]-3-[(2-fluoro-6-methoxy-4-pyridyl)amino]pyrazole-4-carboxamide having at least one of the following characteristics:

an X-ray powder diffraction (XRPD) spectrum having at least one peak in terms of ° 2θ(±0.2) selected from the group consisting of 7.3, 12.6, 12.9, 13.1, 16.2, 17.4, 21.8, 27.8 and 28.4;
   a carbon-13 cross-polarization magic-angle spinning (CP-MAS) nuclear magnetic resonance (NMR) spectrum having at least one peak selected from the group consisting of 29.80, 30.52, 54.35, 60.67, 65.45, 70.62, 89.08, 92.52, 102.17, 121.96, 123.48, 131.05, 152.21, 163.46, 164.53, and 168.40 ppm;
   or
   a differential scanning calorimetry (DSC) thermogram comprising a first endothermic peak with an onset temperature of about 27° C. and a second endothermic peak at about 254° C.

6. The crystalline hydrate form of claim 5, having an X-ray powder diffraction (XRPD) spectrum substantially as shown in FIG. 7.

7. The crystalline hydrate form of claim 5, having carbon-13 cross-polarization magic-angle spinning (CPMAS) nuclear magnetic resonance (NMR) spectrum substantially as shown in FIG. 8.

8. The crystalline hydrate form of claim 5, having a differential scanning calorimetry (DSC) thermogram substantially as shown in FIG. 9.

9. A pharmaceutical composition comprising the crystalline form of claim 1 and a pharmaceutical excipient.

10. The pharmaceutical composition of claim 9, wherein the crystalline form is substantially purified.

11. A method of treating a JAK-mediated disease or condition in a mammal comprising administering the composition of claim 9.

12. The method of claim 11, wherein the JAK-mediated disease or condition is atopic dermatitis.

13. A process for preparing the crystalline form of claim 1 comprising precipitating the crystalline form from a solution of 1-[(3R,4S)-4-cyanotetrahydropyran-3-yl]-3-[(2-fluoro-6-methoxy-4-pyridyl)amino]pyrazole-4-carboxamide and a solvent;

wherein the solution is heated to reflux temperature and then cooled.

14. The process of claim 13, wherein the solvent is selected from the group consisting of methanol, dimethylacetamide, toluene, xylenes, ethyl acetate or mixtures thereof.

15. The process of claim 13, wherein the reflux temperature is between about 60° C. and about 70° C. and the solution is cooled to a temperature of lower then about 25° C.

* * * * *

UNITED STATES PATENT AND TRADEMARK OFFICE
CERTIFICATE OF CORRECTION

| | | |
|---|---|---|
| PATENT NO. | : 12,018,020 B2 | Page 1 of 1 |
| APPLICATION NO. | : 17/311560 | |
| DATED | : June 25, 2024 | |
| INVENTOR(S) | : Chassaing et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this
Fifth Day of November, 2024

Katherine Kelly Vidal
*Director of the United States Patent and Trademark Office*